United States Patent [19]

Harrick et al.

[11] Patent Number: 5,210,418
[45] Date of Patent: May 11, 1993

[54] ULTRA-SMALL SAMPLE ANALYZER FOR INTERNAL REFLECTION SPECTROSCOPY

[75] Inventors: Nicolas J. Harrick, Ossining; Milan Milosevic, Fishkill, both of N.Y.

[73] Assignee: Harrick Scientific Corp., Ossining, N.Y.

[21] Appl. No.: 762,577

[22] Filed: Sep. 19, 1991

[51] Int. Cl.⁵ ............... G01N 21/17; G01N 21/01
[52] U.S. Cl. .................... 250/339; 250/341; 356/244; 356/300
[58] Field of Search ............. 250/339, 340, 341; 356/300, 244, 246, 445, 326

[56] References Cited

U.S. PATENT DOCUMENTS

| | | | |
|---|---|---|---|
| 3,157,788 | 11/1964 | Roche | 356/326 X |
| 3,240,111 | 3/1966 | Sherman et al. | 356/300 |
| 3,478,206 | 11/1969 | Gaglione | 356/246 X |
| 3,486,829 | 12/1969 | Wilks, Jr. | 356/51 X |
| 4,602,869 | 7/1986 | Harrick | 356/244 |
| 5,048,970 | 9/1991 | Milosevic et al. | 356/244 X |
| 5,093,580 | 3/1992 | Sting | 250/445 X |

Primary Examiner—Constantine Hannaher
Assistant Examiner—Edward J. Glick

[57] ABSTRACT

An ultra-small sample analyzer for internal reflection spectrometry comprises a small hemispherical crystal of an infrared-transparent hard material whose flat surface receives the sample to be analyzed. The analyzing beam is contracted to a very small size when incident on the hemispherical surface. Pressure-applying means of a size substantially matching that of the beam at the sampling surface enables interaction of substantially the entire beam with the sample producing spectra of high contrast from microgram or nanogram quantities of the sample.

25 Claims, 14 Drawing Sheets

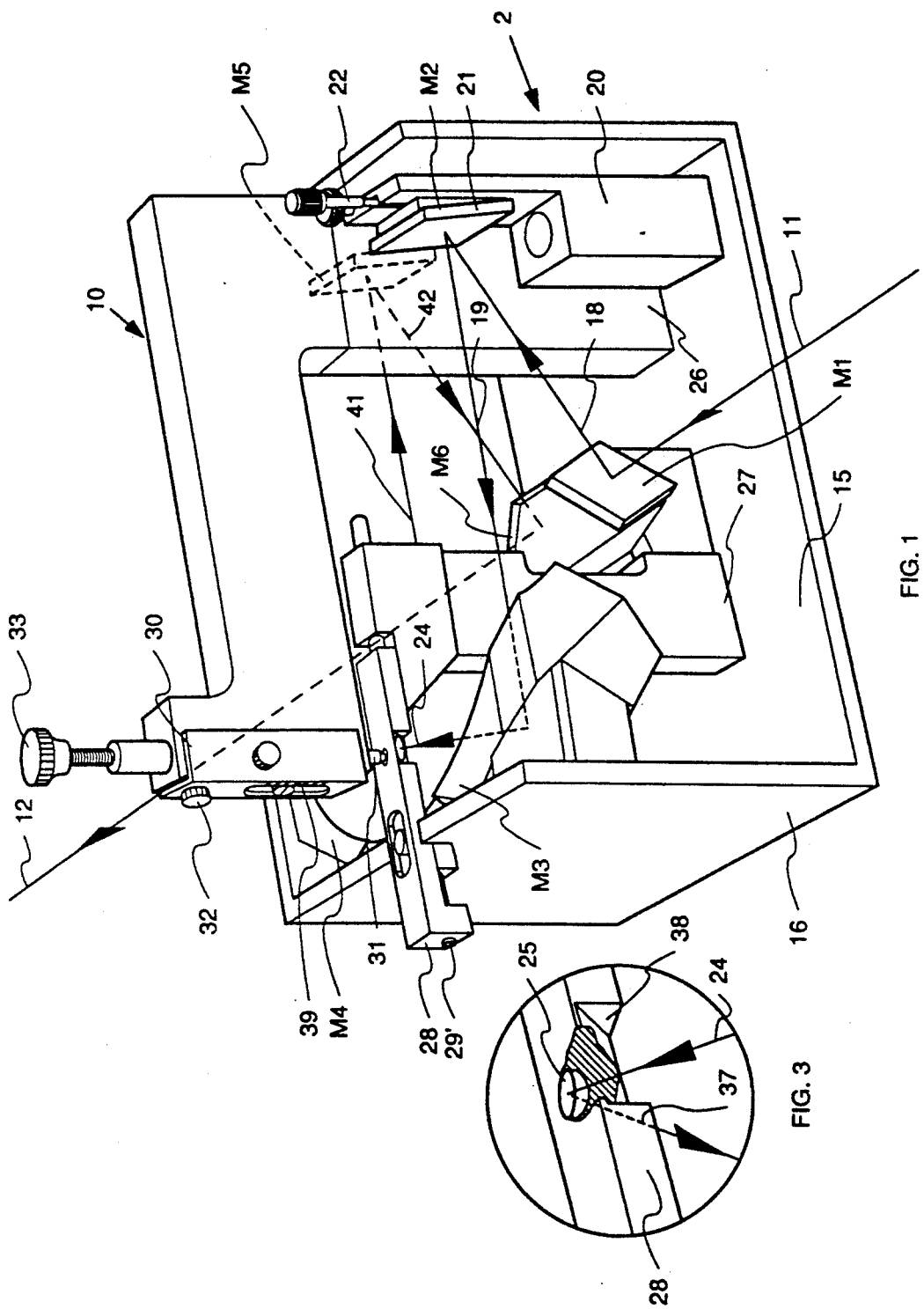

ULTRA-SMALL SAMPLE ANALYZER FOR INTERNAL REFLECTION SPECTROSCOPY

This invention relates to internal reflectance spectroscopic analysis, and in particular to an accessory for use with such a technique for the spectroscopic analysis of physically small samples.

BACKGROUND OF THE INVENTION

Optical spectroscopy is one of the most powerful and widely employed analytical techniques currently in use. There is a universal demand for a non-destructive, spectroscopic probe of samples where only microgram and nanogram quantities are available. Spectra of such samples can be recorded using any of the six major optical spectroscopic techniques. The method most commonly used to obtain spectra of physically small samples is transmission. Both external reflectance and internal reflectance have also been used for microsampling, but the former is limited to examining contaminants on reflective surfaces, and the latter has not yet been fully developed as a reliable technique.

Transmission microsampling, though applicable to a wide variety of samples, has an inherent limitation which restricts the performance of the needed accessories like microscopes, beam condensers, and diamond cells. With this technique, the sample must be optically thin. Many physically small samples are not naturally optically thin and hence must be made so prior to analysis. Samples are typically diluted or physically compressed to produce a concentration or thickness that can be examined by transmission. This process frequently destroys the sample integrity and may produce distortions in the resulting spectrum.

Internal reflectance spectrometry has no such restriction. Since the sample is simply placed in optical contact with a prism, internal reflectance requires little or no sample preparation. The pressures required to achieve good contact in internal reflectance are much lower than those needed to flatten a solid sample for transmission studies and hence would retain the integrity of the sample without special distortions. In addition, internal reflectance can be used to analyze samples that are typically difficult to analyze in transmission, such as opaque substances and films on opaque substrates.

However, to examine physically small samples in internal reflectance, the dimensions of the active portion of the internal reflection element which supports the sample needs to be comparable to the size of the sample. One such internal reflectance accessory has been designed and is currently available from Harrick Scientific Corp. See also U.S. Pat. No. 4,732,475. Known as the Nanosampler, this accessory, while effective for liquids and soft surface solids, utilizes an internal reflection element that fractures easily and has a somewhat obstructed small sampling area, making it difficult to position the sample. These factors make the Nanosampler nearly impossible to use with hard samples which require compression, or on a routine basis.

SUMMARY OF THE INVENTION

The chief object of the invention is an internal reflection nanosampler accessory that not only needs a sampling surface with a size comparable to that of the sample, and using as the internal reflection element a prism fabricated from a durable, hard material, such as silicon or diamond. Since these latter materials have absorbances in the mid-infrared, a further object is a construction in which the beam pathlength through the element is minimized.

In accordance with one aspect of the invention, the accessory comprises a hemisphere as the internal reflection element, with its flat surface serving to support the sample to be analyzed. The radiation beam is incident on a region of the curved surface of the internal reflection element. The result is to contract the beam size where it is incident on the flat surface to a very small value comparable to the nanogram sample to be analyzed.

In accordance with a further aspect of the invention, the hemispherical internal reflection element is supported on a structure which provides ready access to the flat sampling surface. The structure provides overhead a piston type of pressure plate for applying pressure to the sample at a location where the contracted beam intercepts the sampling surface and also of a size that is substantially commensurate with the beam size at that location. As a result, virtually the entire beam can interact with the compressed sample, and thus the resultant strong modulation of the radiation beam when subsequently processed produces excellent spectra of the sample.

The accessory according to the invention not only satisfies the requirements indicated above, but also is capable of low-cost manufacture, simple to operate, and can also be adapted for external or in-line diffuse reflectance for some samples.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a perspective view of one form of ultra-small sample analyzer device according to the invention with several sides of its enclosure removed to show its interior;

FIG. 3 is an enlarged perspective view of the internal reflection element and immediately surrounding structure of the device of FIG. 1;

DETAILED DESCRIPTION OF THE PREFERRED EMBODIMENTS

Figure 1A:
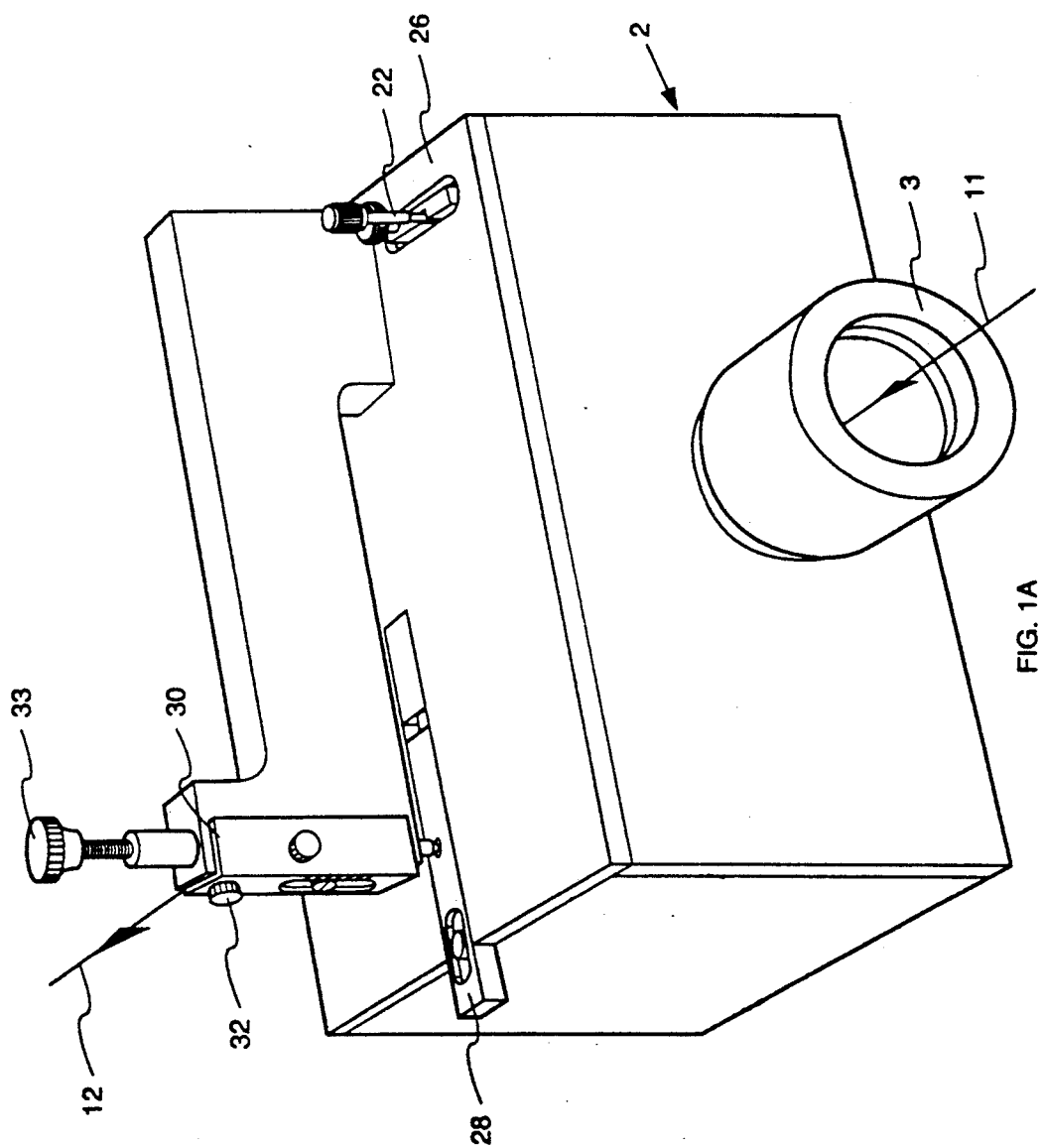
FIG. 1A is a perspective view of the assembled device of FIG. 1.
Figure 2:
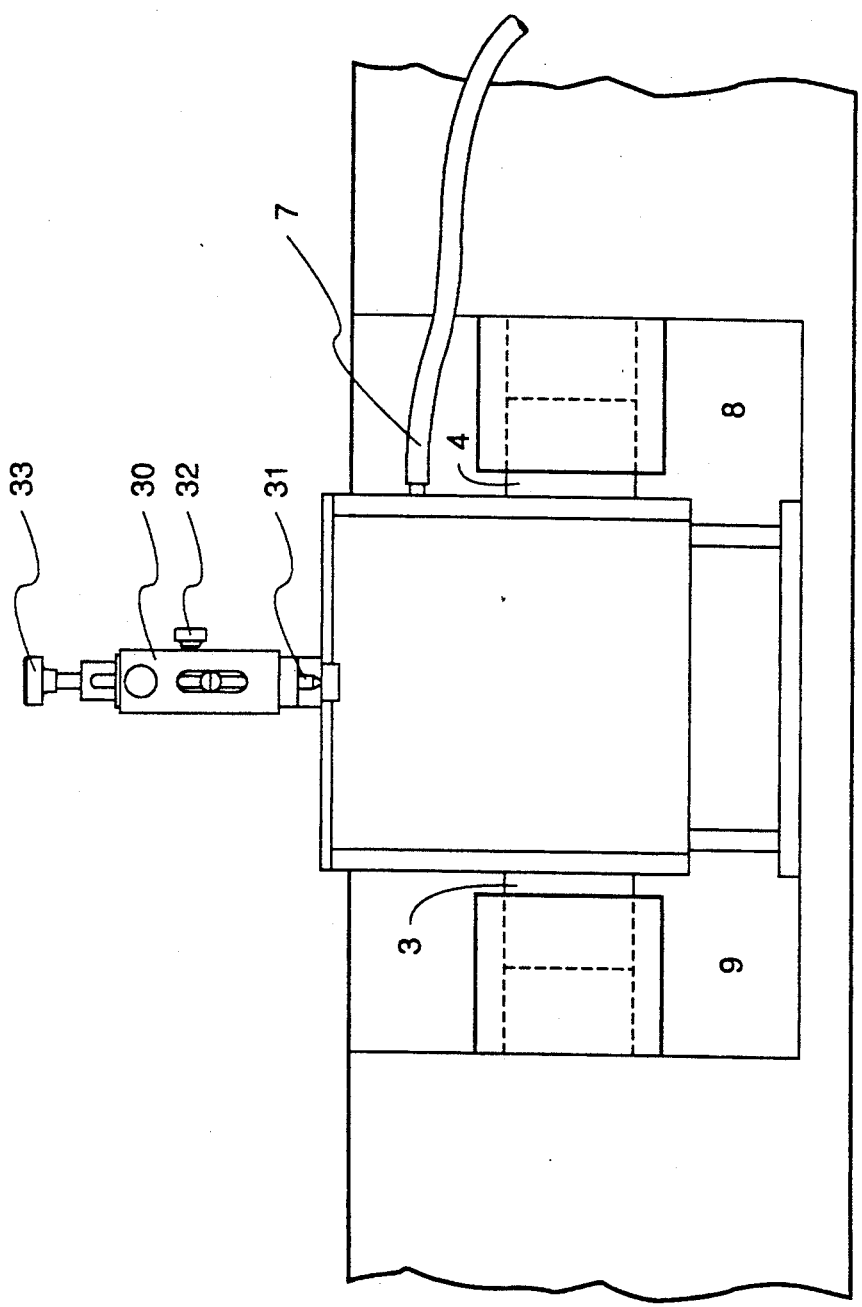
FIG. 2 is an elevational view of the device of FIG. 1A shown seated in the sampling compartment of a spectrometer.

One form of a device 10 according to the invention is illustrated in FIGS. 1 and 1A. It comprises an enclosure 2 forming a closed interior for a purging medium. An inlet 3 allows a radiation beam 11 to enter the enclosure, and an outlet 4 (FIG. 2) allows a radiation beam 12 to exit the enclosure. The purging medium can be provided via a tube 7. As is conventional for such accessories 10, it is adapted to fit within the sampling compartment 8 of conventional optical spectrometers 9. The latter provides a radiation beam in the infrared, visible, or ultraviolet portions of the spectrum. While the ultra-small sample analyzer of the invention can, in principle, be used with visible or ultraviolet radiation, the most common use is with infrared radiation, and the invention will be described in the latter application.

The radiation beam provided by the spectrometer 9, which beam is designated 11, is, in use, typically swept across a range of wavelengths to produce the conventional spectra which plot sample absorbance as a function of wavelength or wavenumber. The beam 11 typically converges to a small area in the sampling compartment and then diverges to form an exiting beam 12 which is received by the spectrometer and processed in the normal manner. If the beam has interacted with a sample, the beam intensity is modulated at wavelengths characteristic of the sample structure. The typical accessory must intercept the entrance beam 11, redirect it to the sample, and then restore the beam leaving the sample to the path it would have followed if the accessory were not present. By proper adjustment of the optical path lengths within the accessory, using proper optical elements, the original focussing conditions can be maintained.

Referring back to FIG. 1, the accessory comprises a base member 15 with side walls 16 (only one of which is shown) for supporting the various optical and physical elements. The optical elements include first and second plane mirrors M1, M2, which direct the entrance beam 11 along a path designated 18, 19 toward a first ellipsoidal mirror M3. The mirror M2 comprises a support 20 for a plane mirror 21, with means 22 for angular and vertical positioning of the mirror 21.

The radiation beam 24 reflected from the ellipsoidal mirror M3 is directed toward a generally U-shaped structure which supports an internal reflection element 25. The support structure comprises a vertical support 27 for a central horizontal bar 28 serving as the hemispherical internal reflection element and sample holder, over which is cantilevered from a vertical support 26 a pressure applying mechanism 30. The pressure applying mechanism 30 comprises a rod-like piston member 31 which is mounted for vertical movement by a user with the mechanism. A knob 32 is used to move the piston 31 up and down, and the pressure applied with the piston 31 in its down pressure-applying position is controlled by an adjustment member 33. A scale 39 is provided to indicate the amount of the pressure. A block with a set screw adjustment 29' is provided to translate the sample holder 28.

Figure 4B:
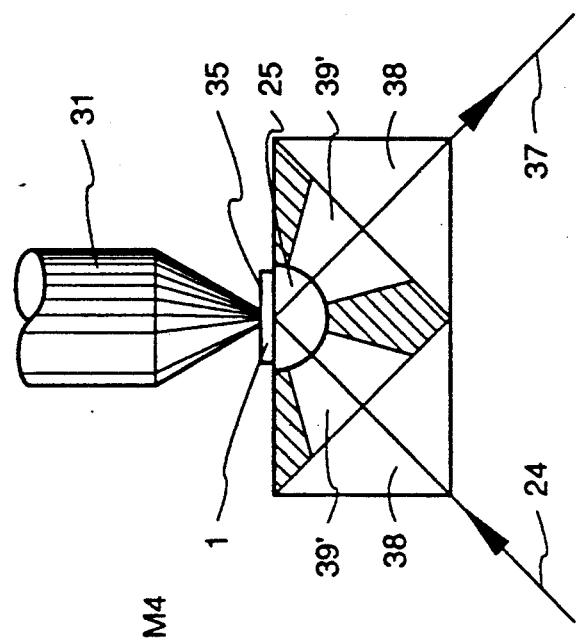
FIG. 4B is an enlarged view of the hemispherical internal reflection element of FIG. 4A.
Figure 5B:
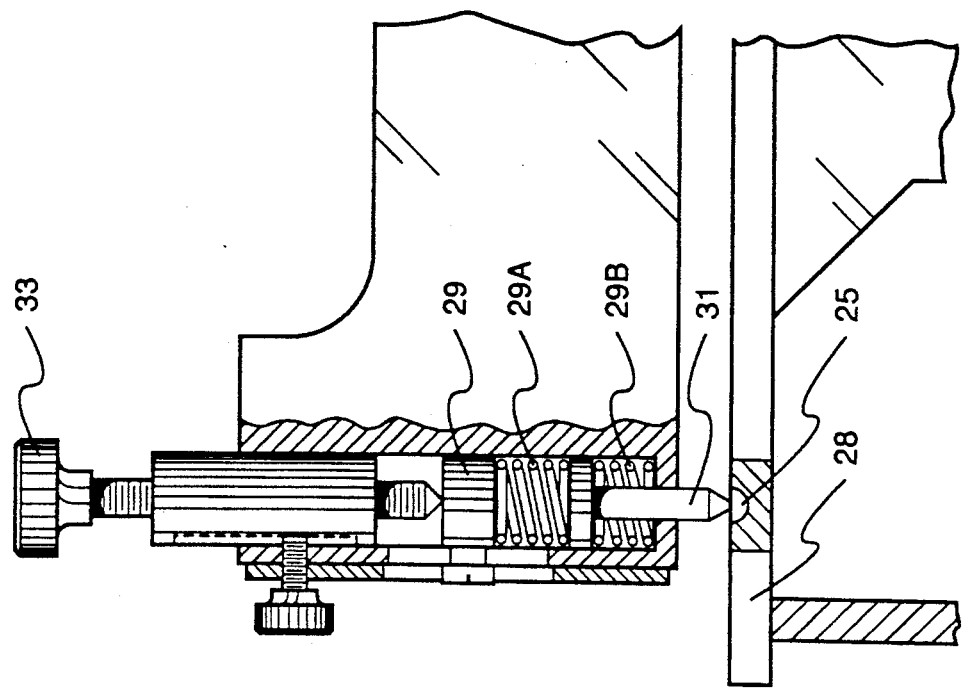
FIGS. 5A and 5B are front and cross-sectional views, respectively, of the pressure-applying mechanism of the device of FIG. 1.
Figure 5A:
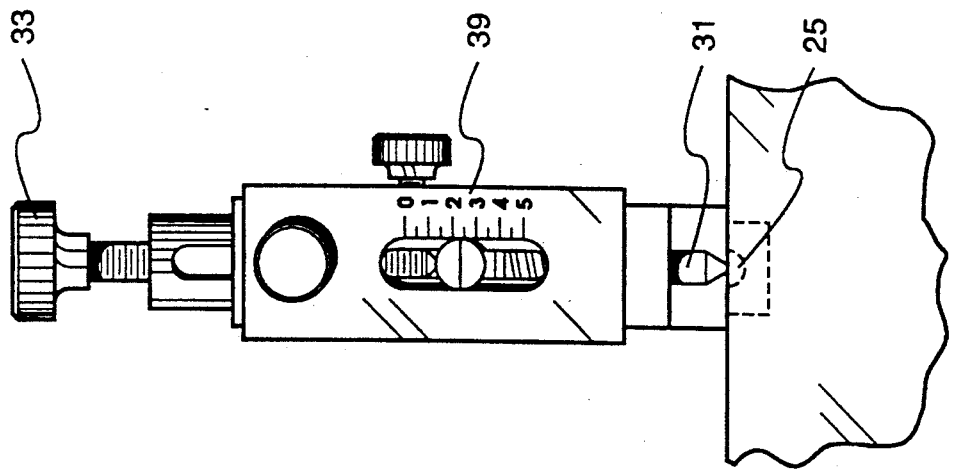

The internal construction is shown in FIGS. 5A and 5B. Rotating the knob 33 presses down on a cylinder 29 which spring loads 29A, 29B the piston 31 which in turn transmits the pressure to the top flat surface of the hemispherical internal reflection element 25. A sample 1 (FIG. 4B) placed between the piston 31 and the hemispherical internal reflection element top surface 35 will thus be compressed, and the amount of that compression is adjustable.

Figure 4A:
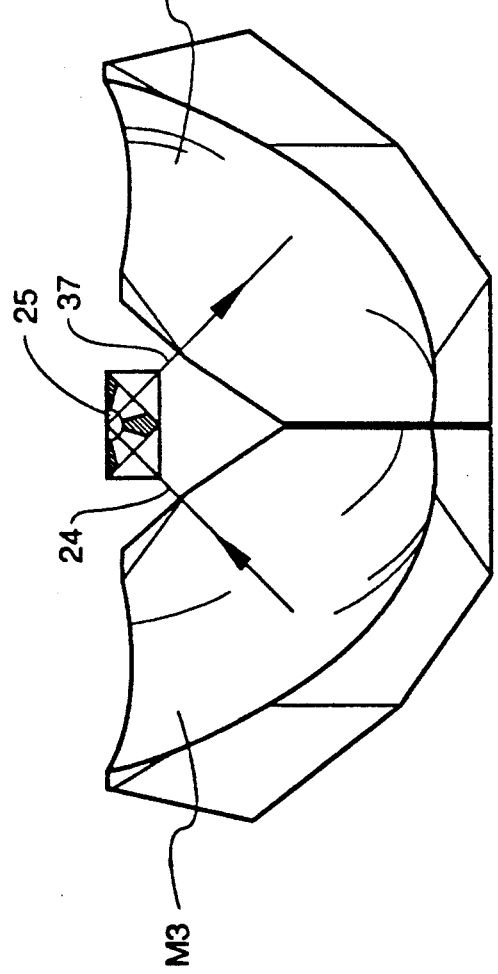
FIG. 4A is a view from the side of the device of FIG. 1 showing the optical geometry of the ellipsoidal reflectors and the hemispherical internal reflection element.

The hemispherical internal reflection element 25 is supported on the horizontal bar 28 (see also FIG. 3) in such manner that its flat sampling surface 35 is flush with or slightly above the upper surface of the bar. The support for the internal reflection element 25 is such that pressure can be applied from the top without displacing the element 25. To provide access for the entering 24 and exiting beams 37, bevelled or conical cut-outs 38 are provided in the bar 28 on opposite sides of the internal reflection element 25 (the cut-out on the back side is not visible in FIGS. 1 and 3). In addition, a hole 39' which passes from the bevelled surface 38 to the spherical surface of the internal reflection element 25 is also provided on opposite sides, as shown more clearly in FIGS. 4A and 4B.

The incident beam 24, internally reflected form the sampling surface 35, exits at 37, reflects off 41 a second ellipsoidal mirror M4, and is directed toward a third plane mirror M5, from which the radiation beam 42 is redirected toward a fourth plane mirror M6, and is thus restored at 12 to the optical path it would have followed had the accessory not been present.

It will be observed that the basic optics is symmetrical about a vertical plane passing through the center of the hemispherical element 25 and the center lines of the posts 26, 27. Thus, the three optical elements M4. M5, and M6 for the exiting beam are a mirror image of the three optical elements M1, M2, and M3 for the entering beam. As previously indicated, the exiting beam 12 goes back into the spectrometer for detection, and the resultant electrical signal processed in the well-known manner.

The hemispherical internal reflection element 25 preferably is a single crystal with a small diameter. Diameters in the range of 2-5 mm can be used. A hemispherical internal reflection element with a 3 mm diameter is preferred. This short (3 mm) pathlength through the crystal 25 broadens the choice of optical materials for the internal reflection element 25 to include those listed in Table 1 below:

TABLE 1

| Material | Refractive Index | Hardness (Knoop) | Useful Range for 3 mm path (cm$^{-1}$) |
|---|---|---|---|
| Diamond | 2.4 | 7000 | 45,000–2500, 1600-FIR |
| Germanium | 4.0 | 550 | 5000–600 |
| Silicon | 3.42 | 1150 | 10,000–100 |
| Zinc Selenide | 2.42 | 150 | 20,000–500 |
| Zirconium Dioxide | 2.15 | 1250 | 27,000–1500 |

For this pathlength, silicon, for example, is essentially transparent to the far and mid-infrared. Silicon is particularly useful as the internal reflection element 25 in the accessory according to the invention. It is a hard material, permitting the application of high clamping pressures to ensure good contact between the crystal and the sample; it is extremely inert, allowing analyses of highly corrosive materials; and it has a high refractive index, providing a high degree of beam condensation, as discussed below. In addition, silicon is a relatively low-cost material.

Figure 6B:
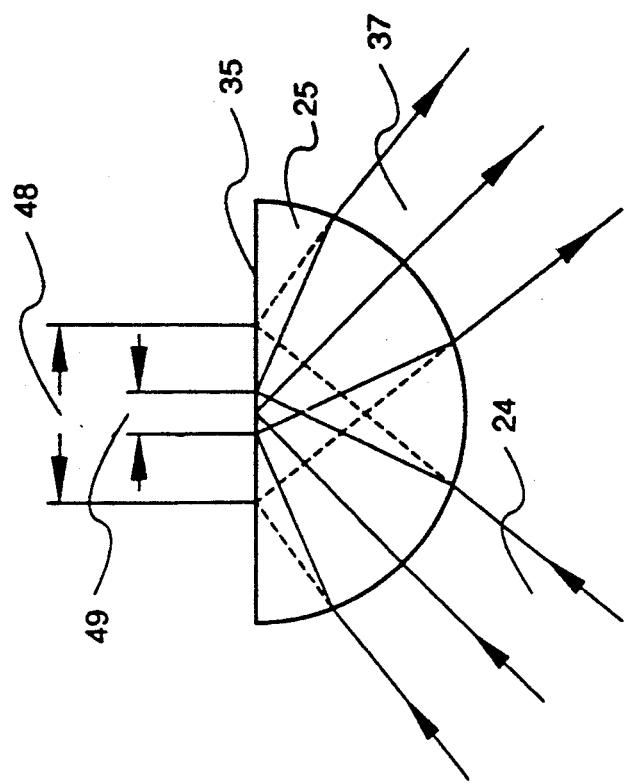
FIGS. 6A and 6B are schematic optical views, for comparison purposes, of a prism and of a hemispherical internal reflection element according to the invention.
Figure 6A:
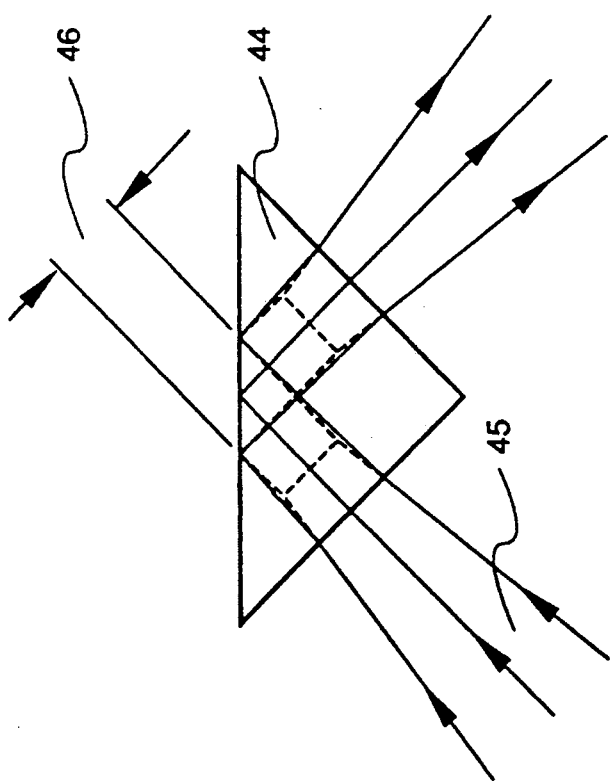

A feature of the invention is that the hemispherical geometry of the internal reflection element 25 demagnifies or concentrates the incident radiation onto the sample, in addition to the demagnification provided by the ellipsoidal mirror M3. The radiation transmitted through the interface of two transparent media is refracted according to Snell's Law. For a triangular prism 44 (see FIG. 6A), this results in defocusing, i.e., the non-central rays of a converging beam 45 are spread over a wider angle than the beam impinging on the prism. The beam size 46 at the upper horizontal surface is no different from that at the entering surface below. The converging action of the incident beam 45 is lost. For a hemisphere 25 according to the invention (FIG. 6B), however, refraction of the converging beam 24 at the interface focuses as shown by the solid lines, providing n times linear reduction of the source image, where n is the refractive index of the crystal. In FIG. 6B, 48 designates the original beam size at the interface, following the dashed lines, and 49 designates the contracted beam size at the sampling surface 35. Thus, using a microhemisphere in the accessory according to the invention produces an effective sampling surface 49', corresponding to the contracted beam size 49, with a diameter that is 6n times smaller than that of the infrared beam of the spectrophotometer. Preferably, the optics are configured such that the sampling area, i.e., the effective sampling surface 49', has a diameter of about 1 mm or less.

Such a sampling area is most useful when the sample can be properly located on and clamped against the internal reflection element 25. The pressure plate formed by the tapered tip of the piston 31 of the pressure mechanism 30 is configured and mounted to cover only the small sampling area 49' of the crystal. This not only increases the achievable clamping pressures, but also reduces the problems associated with positioning small samples. For the same force applied, higher contact pressures can be achieved with a small pressure plate than with a large one. This is particularly for hard and slightly curved or roughened samples, where higher pressures are required to produce the good contact needed for reproducible spectra. However, the pressure plate area should not be smaller than the sampling area 49'. If the sampling area 49' of the crystal 25 is not covered completely, some of the incident radiation is reflected without interacting with the sample, resulting in reduced spectral contrast. Thus, the most effective pressure plate is substantially matched to the size of the sampling area 49' also referred to as the "hot spot". This is readily achieved as shown by tapering or bevelling the point at the bottom of the piston 31. Since the piston point does not actually touch the sampling surface, it is out of range of the beam's evanescent wave. Hence, the piston point can be made of any suitable material, such as Delrin plastic.

In order to fabricate a pressure plate which covers the active portion of the internal reflection element, the size of the hot spot must be known. The size of the sampling area can be easily experimentally determined. To measure the sampling area 49' a hard plastic pin, made of Delrin plastic, is bevelled to a 0.1 mm diameter tip and placed at various locations on the sampling surface of the hemisphere. The absorbance of the Delrin transition at 898.4 cm$^{-1}$ is recorded at each position. The Delrin pin is mounted on an X-Y-Z translation stage for precision positioning and data points are collected at 0.127 mm intervals in the X-Y plane. To reduce damage to its point, the Delrin pin can be lifted from the surface 35 of the internal reflection element 25 between measurements. During each measurement, the pin is held in place by the spring pressure of the Z translation stage. This assures reproducible contact pressure between the Delrin and the internal reflection element.

Figure 6C:
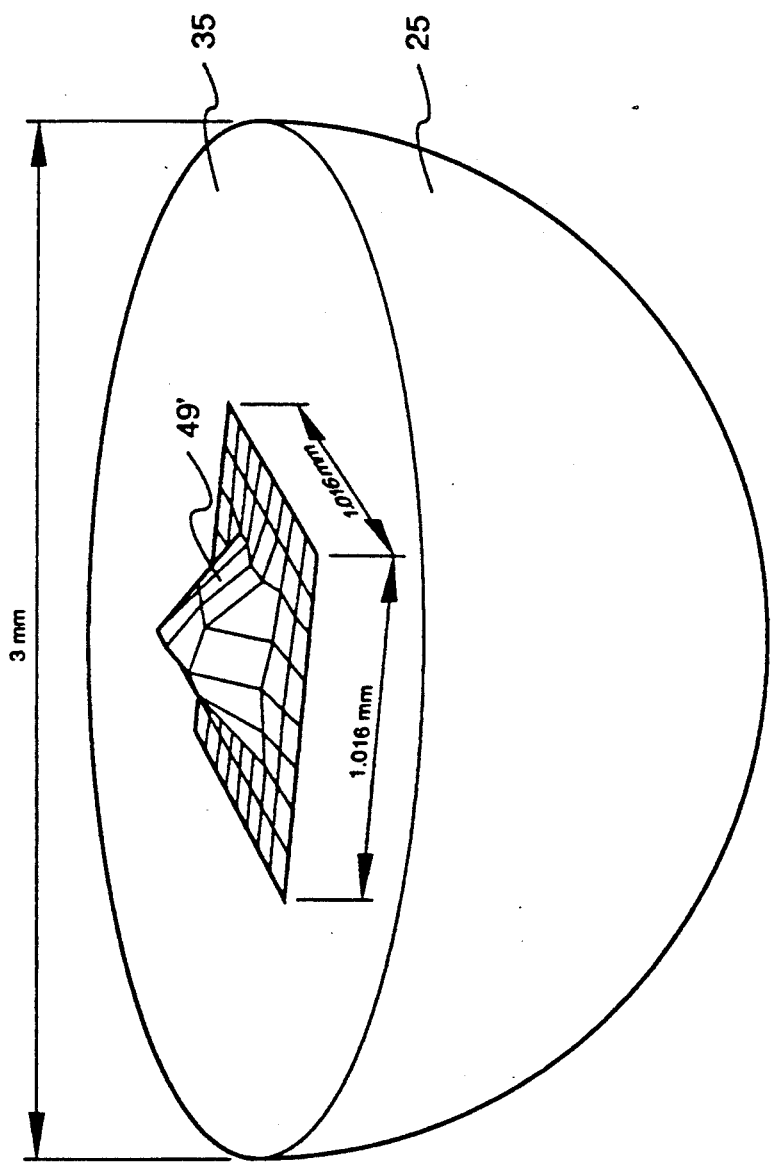
FIG. 6C is an enlarged perspective view of the hemispherical internal reflection element of the device according to the invention showing the optical beam distribution at the sampling surface.

The results described below were obtained with the accessory 10 used in conjunction with a Nicolet 740 FT-IR spectrophotometer. The measured profile of the sampling area 49' is shown in FIG. 6C. This profile was measured on a silicon micro-hemisphere of 3 mm diameter. According to the experimental profile, the accessory 10 has a hot spot 49' with a diameter of about 0.50 mm. Theoretically, with a Si hemisphere, the accessory provides a 20.5 times linear beam condensation. Since the beam diameter at the focus with no accessory in the sample compartment of the spectrometer is approximately 6 mm, the sampling area should have a diameter of roughly 0.3 mm. It is not surprising that the measured hot spot is somewhat larger than theoretically predicted. The Delrin pin had a diameter of approximately 0.1 mm and may have been further flattened due to contact with the internal reflection element. This area was not taken into account in the estimation of the diameter of the sampling area and hence contributes to the difference between the experimental and theoretical diameters.

Another approach can also be used to estimate the size of the hot spot. The ratio of the peak intensity for a sample that partly covers the hot spot to the intensity of a sample of the same material that completely covers the hot spot is directly proportional to the fraction of the hot spot covered. The peak intensities were recorded for a 0.152 mm thick sheet of polyethylene terephthalate (PET) which completely covered the Si internal reflection element, and for a 20 μm PET fiber placed across the center of the crystal in two positions. The results are shown in Table 2 below, where fiber A was positioned perpendicular to the direction of propagation of the beam and fiber B was parallel to it:

TABLE 2

| Sample | % Reflectance (1713 cm$^{-1}$) | Notes |
|---|---|---|
| Sheet | 51.9 | Hemisphere Completely Covered |
| Fiber A | 76.2 | ⊥ to Direction of Beam Propagation |
| Fiber B | 68.9 | ‖ to Direction of Beam Propagation |

If the hot spot is circular and the fiber was compressed to a thickness of no less than 5 μm, giving a width of 60 μm, then the estimated diameter of the hot spot is 0.12 mm. This is smaller than the theoretical diameter. However, the theoretical value neglects vignetting of the beam by the crystal holder and distortions of the beam due to imperfect focusing by the ellipsoids and the hemisphere.

Figure 7:
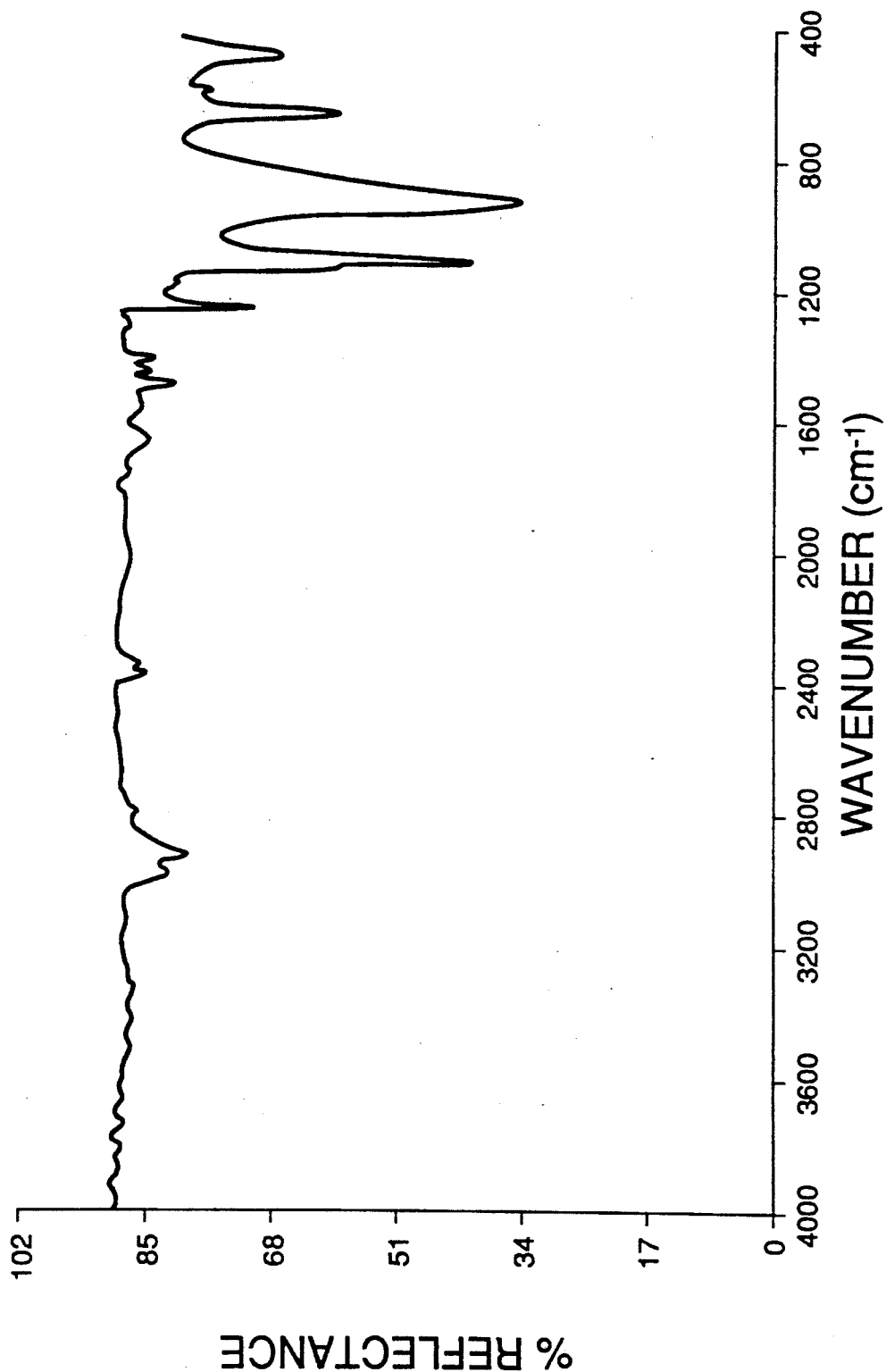
FIGS. 7-13 are spectra of various samples taken with the device of FIG. 1.
Figure 8:
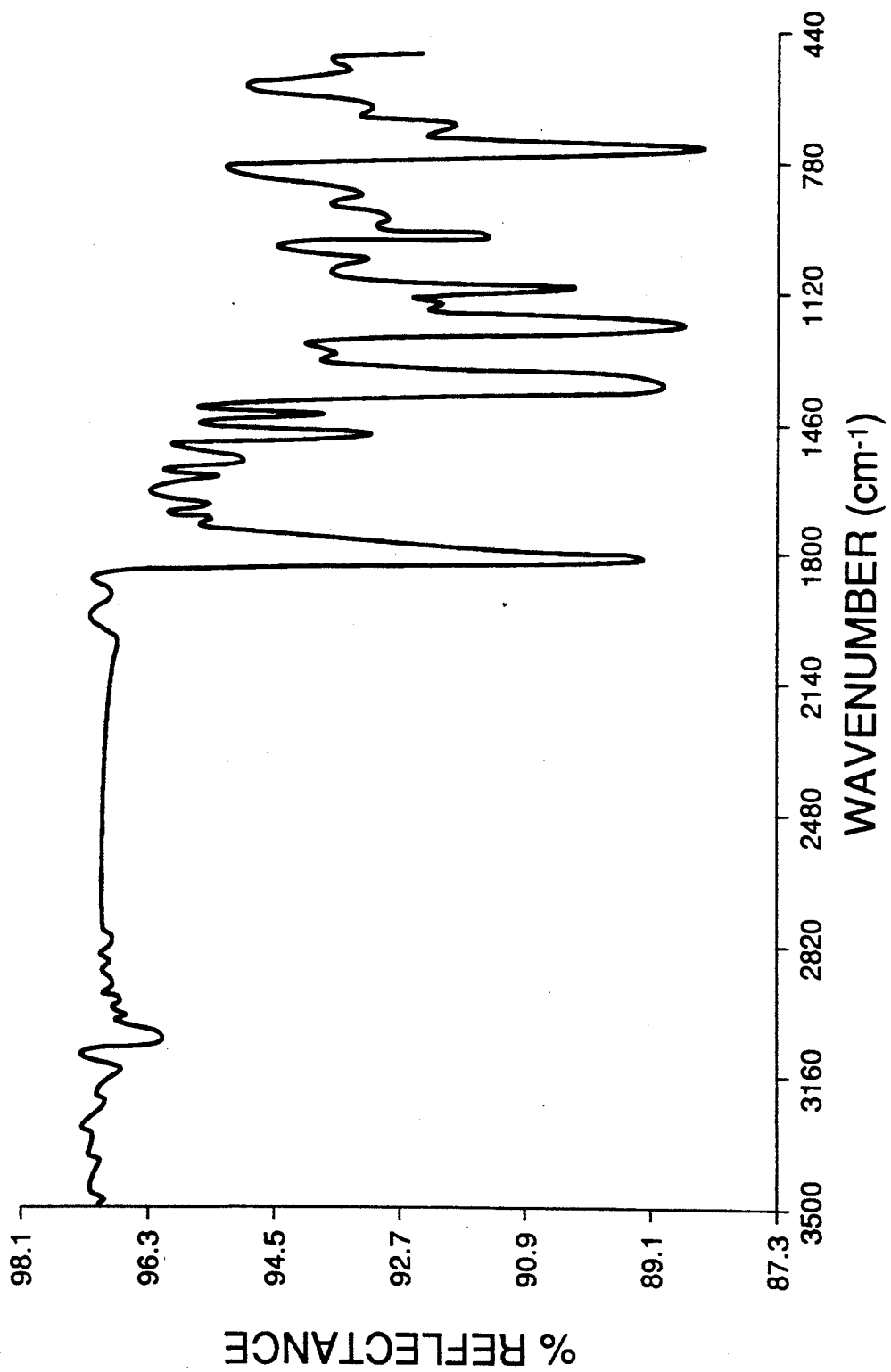
Figure 9:
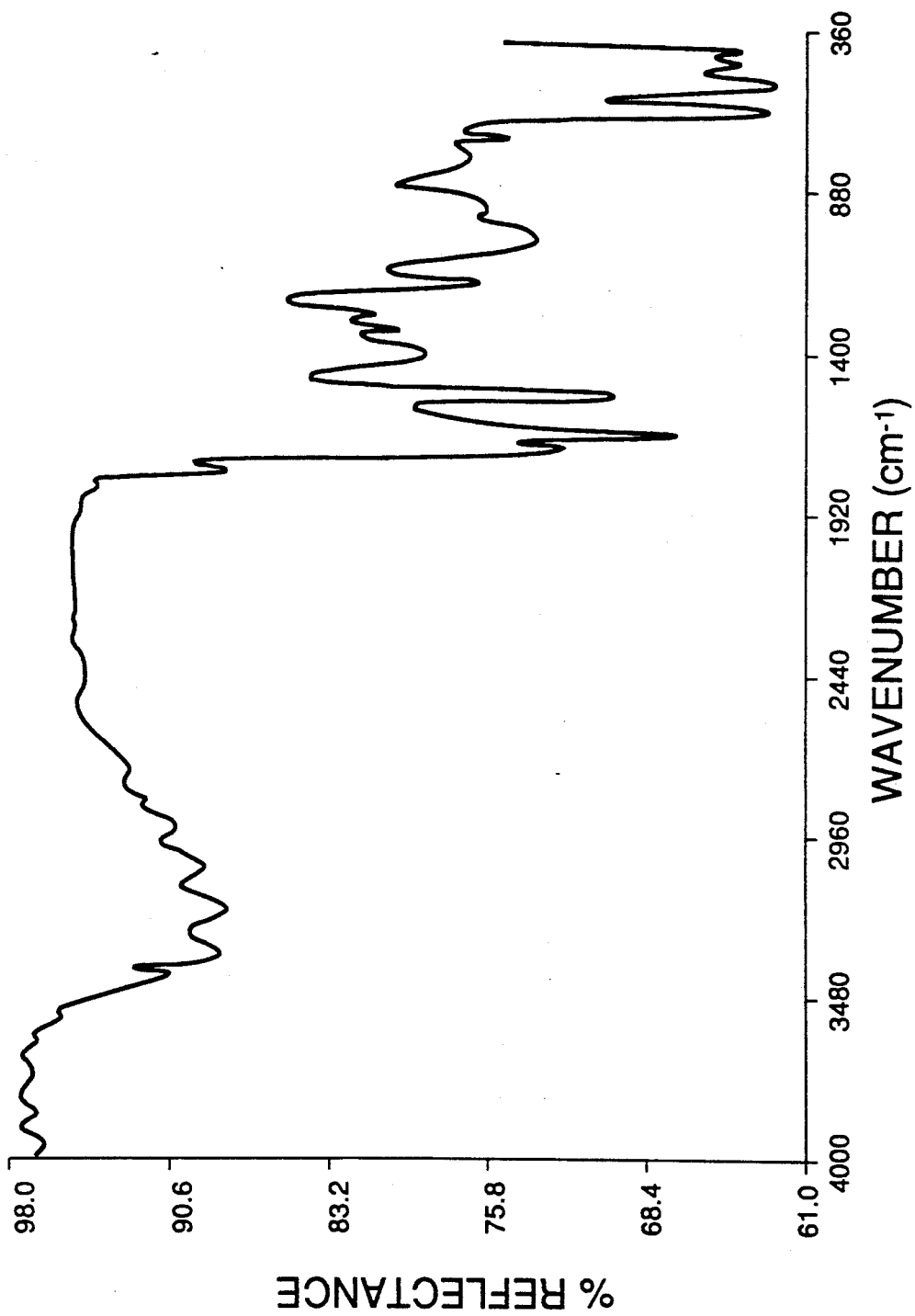

The small size of the sampling area makes it possible to analyze physically small samples as demonstrated by the spectra shown in FIGS. 7–9. FIG. 7 is the internal reflection element of 0.25 × 1.25 mm fragment of a hard plastic, Delrin. FIG. 8 shows the internal reflectance of a 20 mm μm PET, and FIG. 9 is the internal reflection spectrum of a fly speck on a glass slide. The spectra of FIGS. 7 and 9 were obtained using a Si hemispherical internal reflection element, while the spectrum of FIG. 8 was recorded with a ZnSe hemisphere.

Figure 10:
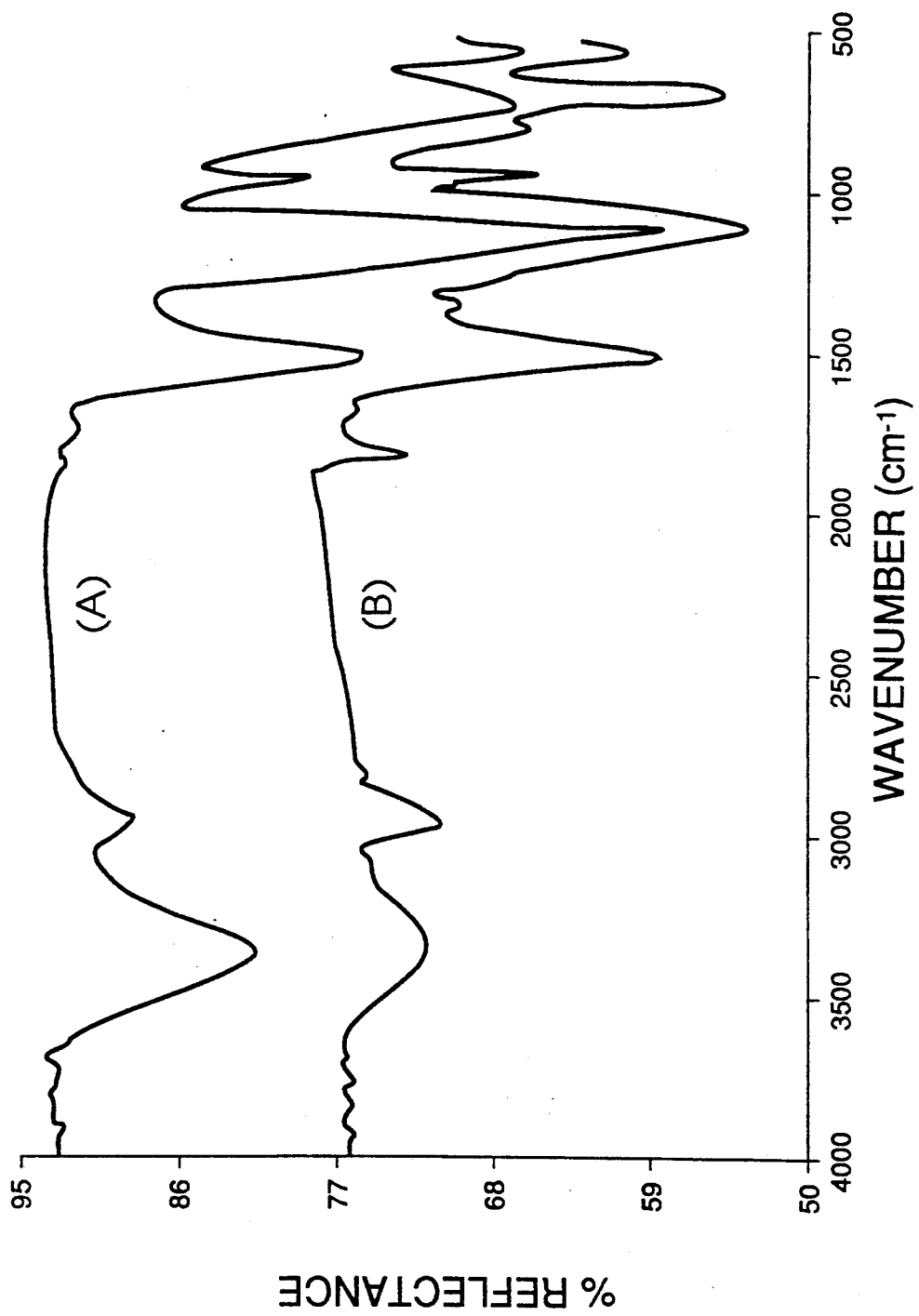

Similarly, small spots on large panels can be examined using the accessory according to the invention. FIG. 10 shows (curve (b)) the internal reflection spectrum of the ink-printed letter 'c' from the middle of an 11"×15" sheet of paper and, for comparison purposes (curve (a)), the spectrum of the paper. Note the emergence of the C-H band relative to the O-H band in the spectrum of ink on paper.

Figure 11:
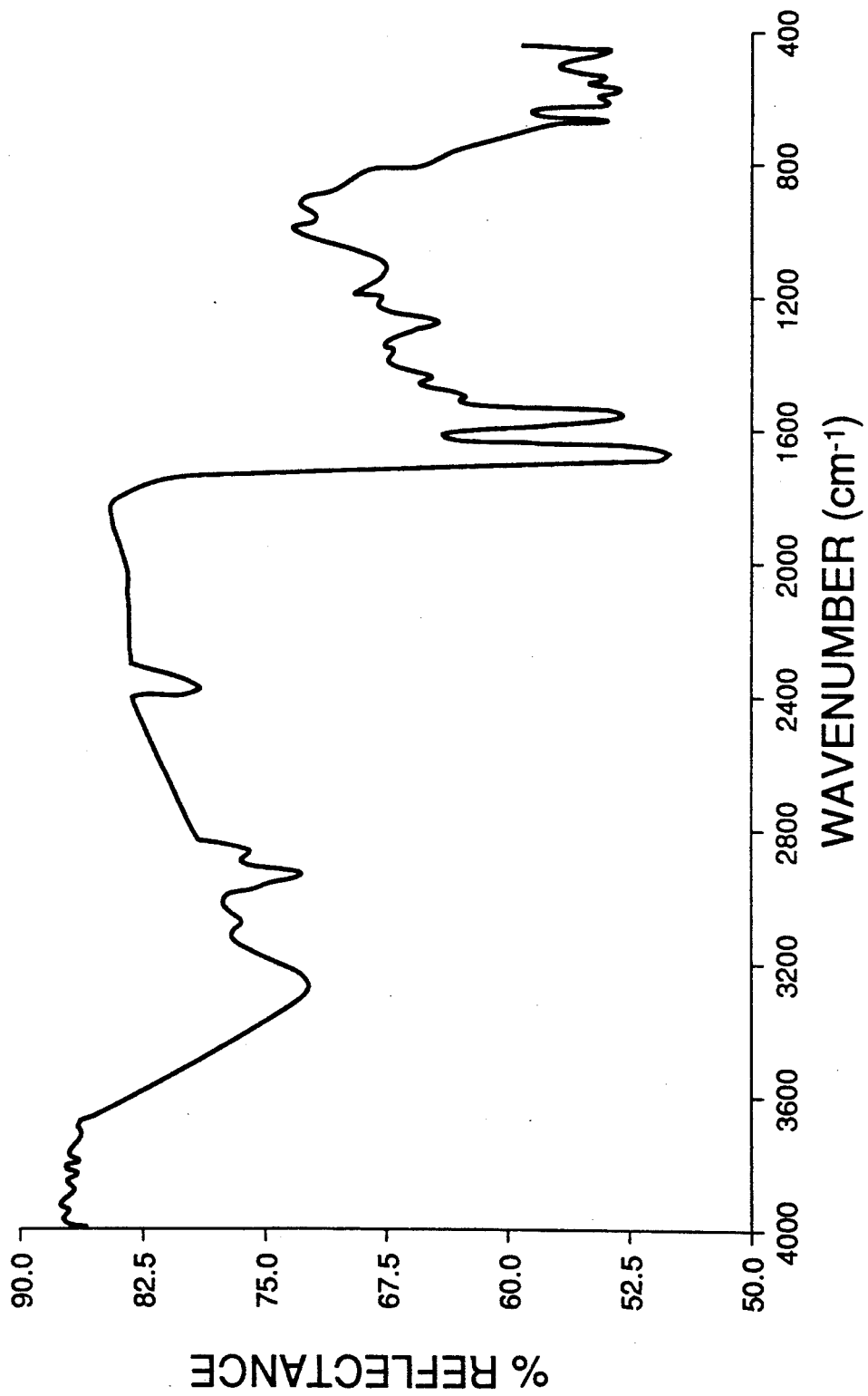

In addition to small samples, materials which are difficult to examine due to sample form can be analyze quickly and easily with the accessory according to the invention. Hard, fibrous samples, such as hair, are typically examined by compressing the sample in a diamond cell and then measuring the spectrum by transmission. Thus, use of the diamond cell requires both destruction of the sample and sample preparation. In contrast, the accessory according to the invention minimizes damage to the sample and preparation of the sample. FIG. 11 shows the spectrum of a single strand of human hair obtained with this new accessory using a Si internal reflection element. Note that both the surface oils on the hair and the underlying fiber are apparent.

Figure 12:
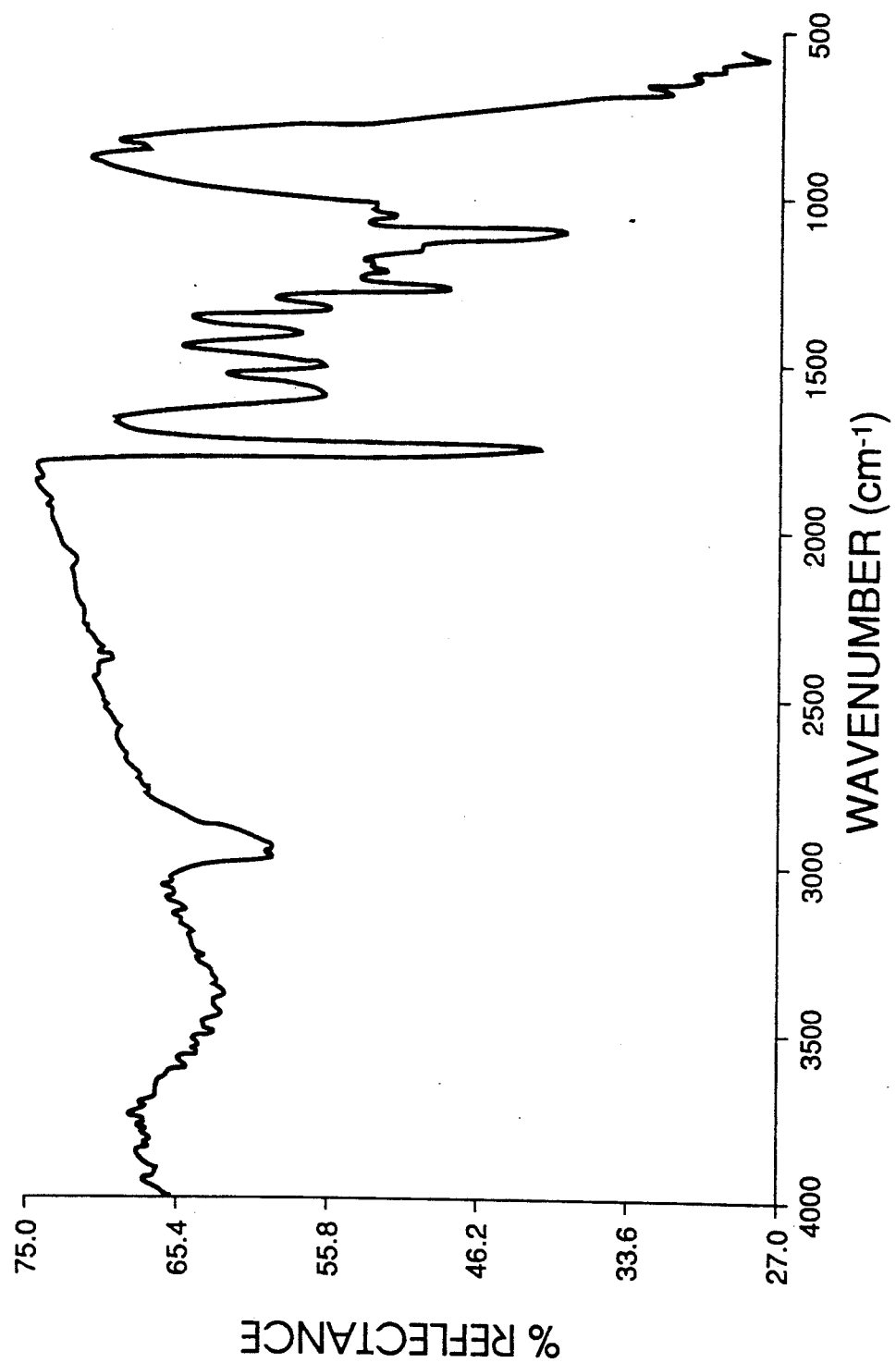

Other samples that are difficult to analyze include fragments of hard, somewhat curved materials, such as paint chips. Compressing or slicing the sample for examination by transmission spectroscopy is more likely to result in the formation of a powder than of a thin film. The powder could be examined by diffuse reflection or transmission upon dilution, but, again, the sample has to be destroyed and then undergo preparation prior to analysis. With its small sampling area and pressure applicator, samples can be flattened against the internal reflection element 25 of the accessory according to the invention while maintaining sample integrity. FIG. 12 shows the spectrum of a chip of automobile paint obtained with this new accessory using a Si internal reflection element.

Figure 13:
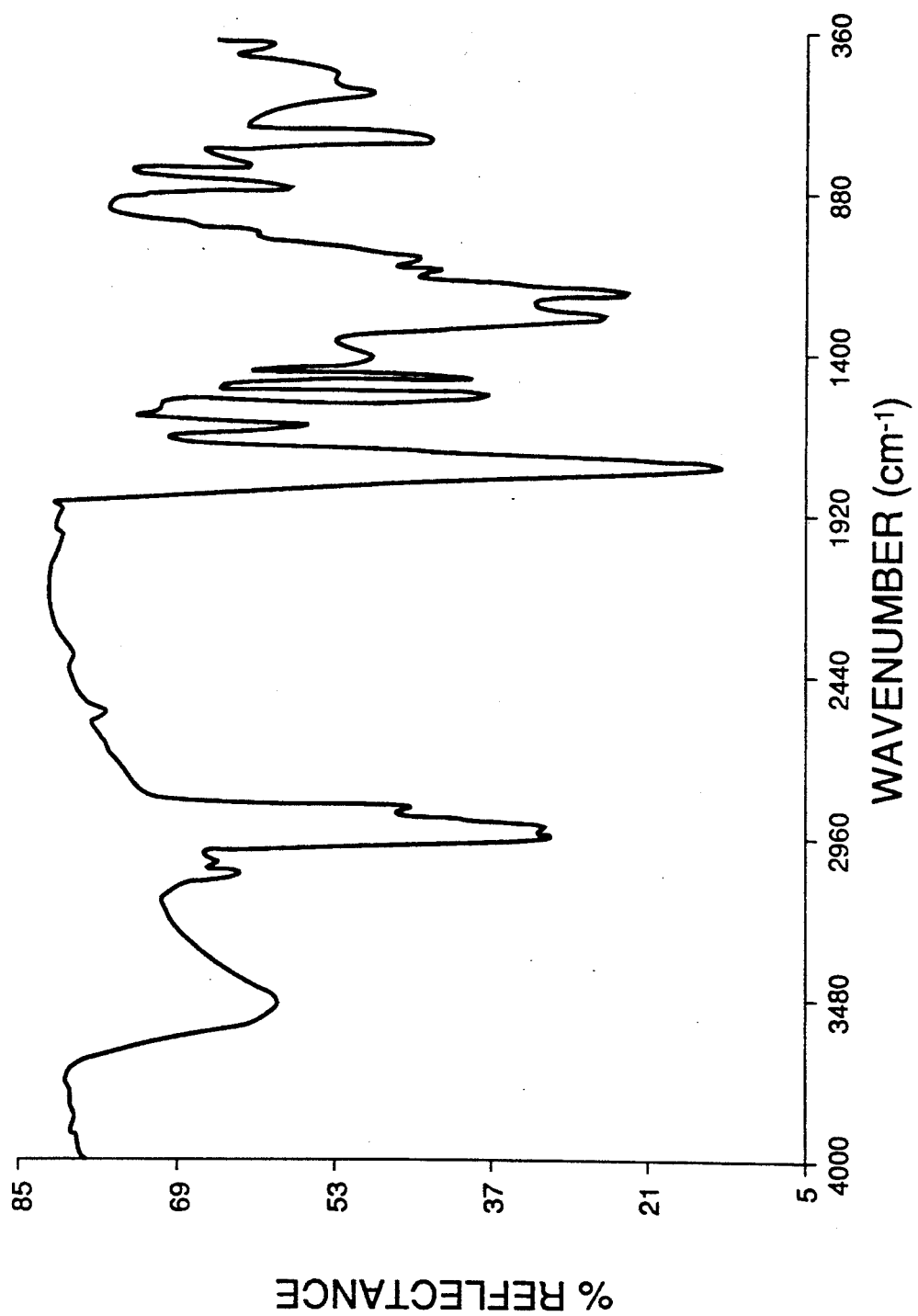

Although the accessory according to the invention is intended primarily for internal reflectance studies of small samples, it can easily be adapted for external or in-line diffuse reflectance. For internal reflectance, the hemispherical internal reflection element 25 is mounted such that its sampling surface 35 lies at the focal plane of the optics, and the sample rests directly above and in contact with the crystal. For external or diffuse reflectance, the internal reflection element is removed and the sample is simply placed upside-down on a suitable holder and thus positioned at the focal plane over the hole previously occupied by the hemisphere. In both configurations, the sampling surface is horizontal and unobstructed, permitting analysis of physically small samples in addition to small portions of large samples, e.g., panels. FIG. 13 shows the external reflection spectrum of the inked portion of a lottery ticket coated with a silver latex layer. Note that the reflectance measured contains both specular and diffuse components.

In summary, a new accessory for the spectroscopic analysis of physically small samples mainly via internal reflectance has been provided which offers several advantages over ones currently in use, such as high pressure diamond cells, microscopes, and beam condensers. It enables non-destructive, internal reflectance studies of microgram and nanogram samples with little or no sample preparation. Moreover, its specially configured pressure plate permits the application of high clamping pressures between the sample and the internal reflection element, simplifying the analysis of hard surface solids such as fibers. It is a very versatile accessory capable not only of internal reflectance, but also of external and diffuse reflectance studies.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An accessory for internal reflection spectroscopy over a useful range of wavelengths, comprising:
   (a) an accessory support,
   (b) an internal reflection element serving as a sample holder on said support, said internal reflection element comprising a hard, substantially radiation transparent, hemispherical crystal having an exposed flat sampling surface area for receiving a sample to be analyzed,
   (c) means on the support for directing an incident beam of radiation containing wavelengths in the useful range onto a portion of the hemispherical surface of the crystal such that the beam internally reflects from the crystal's sampling surface area, said reflected beam exiting the crystal via a portion of the hemispherical surface,
   (d) means on the support for receiving and redirecting the exiting reflected beam,
   (e) said hemispherical crystal being of a material having an absorption band in the said useful range of wavelengths, but having a diameter so small that the resultant small path length for the beam in the crystal results in an insignificant amount of absorption of radiation in the useful range passing through the crystal.

2. The accessory of claim 1, further comprising means on the support for applying pressure against a sample located on the crystal's sampling surface area.

3. The accessory of claim 2, wherein the crystal is selected from the group consisting of diamond, silicon, zinc selenide, and zirconium dioxide.

4. The accessory of claim 2, wherein the crystal is silicon.

5. The accessory of claim 2, wherein the pressure applying means has a tip whose size is substantially matched to the size of the radiation beam at the sampling surface area.

6. The accessory of claim 5, wherein the size of the radiation beam at the sampling surface area is about 1 mm or less.

7. The accessory of claim 5, wherein the tip of the pressure applying means has a size of about 1 mm or less.

8. The accessory of claim 1, wherein the incident beam includes infrared radiation, and the crystal diameter is between about 2-5 mm.

9. The accessory of claim 8, wherein the crystal diameter is about 3 mm.

10. The accessory of claim 1, wherein the crystal has a high index of refraction exceeding 3.

11. An accessory for internal reflection spectroscopy, comprising:
   (a) an accessory support,
   (b) an internal reflection element serving as a sample holder on said support, said internal reflection element comprising a hard, substantially radiation transparent, hemispherical crystal having an exposed flat sampling surface area for receiving a sample to be analyzed,
   (c) means on the support for directing an incident beam of radiation along a first path onto a first portion of the hemispherical surface of the crystal such that the beam internally reflects from the crystal's sampling surface, said reflected beam exiting the crystal via a second portion substantially different from the first portion of the hemispherical surface, (d) means on the support for receiving and redirecting the exiting reflected beam along a second path spaced from the first path.

12. An accessory for internal reflection spectroscopy, comprising:

(a) an enclosure including an accessory support and having spaced inlet and outlet ports, (b) an internal reflection element serving as a sample holder on said support, said internal reflection element comprising a hard, substantially radiation transparent, hemispherical crystal having an exposed flat sampling surface area for receiving a sample to be analyzed, said sampling surface area lying exposed and unobstructed on an upper surface of the enclosure and facing upward, (c) means within the enclosure for directing an incident beam or radiation received through the inlet port onto a portion of the hemispherical surface of the crystal such that the beam internally reflects from the crystal's sampling surface, said reflected beam exiting the crystal via a portion of the hemispherical surface, (d) means within the enclosure for receiving and redirecting the exiting reflected beam to and through the outlet port.

13. The accessory of claim 12, wherein the enclosure is sealed off allowing the enclosure interior to be purged and remain purged while different samples to be analyzed are provided on the sampling surface.

14. The accessory of claim 13, wherein means are provided mounted on the outside of the enclosure and overlying the sampling surface for applying pressure to a sample on the sampling surface.

15. The accessory of claim 14, wherein the pressure applying means comprises means for raising and lowering a rod-like pressure plate, and means for controlling the pressure of the pressure plate on a sample on the sampling surface.

16. The accessory of claim 15, wherein the pressure-applying means comprises a piston, and means for spring-loading the piston.

17. The accessory of claim 14, further comprising a scale for indicating the amount of pressure applied.

18. The accessory of claim 12, wherein the means of elements (c) and (d) each include an ellipsoidal mirror.

19. The accessory of claim 18, wherein the means of elements (c) and (d) each include at least one plane mirror.

20. An internal reflecting spectrophotometer comprising:

(a) a source of converging infrared radiation, (b) a sampling compartment into which the beam is received, (c) an accessory having an enclosure and located in said sampling compartment, (d) an internal reflection element serving as a sample holder and provided in said enclosure, said internal reflection element comprising a hard, substantially infrared radiation transparent, hemispherical crystal having an exposed flat sampling surface area for receiving a sample to be analyzed, said sampling surface area being accessible from outside the enclosure, (e) means in the enclosure for directing an incident beam of radiation onto a portion of the hemispherical surface of the crystal such that the beam internally reflects from the crystal's sampling surface area, said reflected beam exiting the crystal via a portion of the hemispherical surface, (f) means on the enclosure for applying pressure against a sample located on the crystal's sampling surface such that the reflected beam is modulated by interaction with the compressed sample, (g) means for processing the modulated beam to produce a spectrum of beam attenuation vs. wavelength, (h) means in the enclosure for receiving and redirecting the exiting reflected beam to the processing means, (i) said crystal being of silicon and having a diameter between about 2-5 mm.

21. The spectrophotometer of claim 20, wherein the crystal diameter is about 3 mm.

22. The spectrophotometer of claim 20, wherein the pressure applying means has a tip whose size is substantially matched to the size of the radiation beam at the sampling surface area.

23. An accessory for internal reflection spectroscopy, comprising:

(a) an accessory support, (b) an internal reflection element serving as a sample holder on said support, said internal reflection element comprising a hard, substantially radiation transparent, hemispherical crystal having an exposed flat sampling surface for receiving a sample to be analyzed, (c) means on the support for directing an incident beam of radiation onto a portion of the hemispherical surface of the crystal such that the beam internally reflects from the crystal's sampling surface, said reflected beam exiting the crystal via a portion of the hemispherical surface, (d) means on the support for receiving and redirecting the exiting reflected beam, (e) means on the support for applying pressure against a sample located on the crystal's sampling surface, the pressure applying means having a tip whose size is substantially matched to the size of the radiation beam at the sampling surface.

24. The accessory of claim 23, wherein the tip of the pressure applying means has a size of about 1 mm or less.

25. An internal reflecting spectrophotometer comprising:

(a) a source of converging infrared radiation, (b) a sampling compartment into which the beam is received, (c) an internal reflection element serving as a sample holder and provided in said sampling compartment, said internal reflection element comprising a hard, substantially infrared radiation transparent, hemispherical crystal having an exposed flat sampling surface for receiving a sample to be analyzed.

(d) means in the sampling compartment for directing an incident beam of radiation onto a portion of the hemispherical surface of the crystal such that the beam internally reflects from the crystal's sampling surface, said reflected beam exiting the crystal via a portion of the hemispherical surface, (e) means for applying pressure against a sample located on the crystal's sampling surface such that the reflected beam is modulated by interaction with the compressed sample, the pressure applying means having a tip whose size is substantially matched to the size of the radiation beam at the sampling surface, (f) means for processing the modulated beam to produce a spectrum of beam attenuation vs. wavelength.

(g) means in the sampling compartment for receiving and redirecting the exiting reflected beam to the processing means.

* * * * *